(12) United States Patent
Roach et al.

(10) Patent No.: US 6,627,446 B1
(45) Date of Patent: *Sep. 30, 2003

(54) ROBOTIC MICROCHANNEL BIOANALYTICAL INSTRUMENT

(75) Inventors: David J. Roach, Los Gatos, CA (US); Robert T. Loder, Jr., Sunnyvale, CA (US); Thomas M. Armstrong, Palo Alto, CA (US); Dennis W. Harris, Buckinghamshire (GB); Stevan B. Jovanovich, Livermore, CA (US); Richard F. Johnston, Murphys, CA (US)

(73) Assignee: Amersham Biosciences (SV) Corp, Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/109,676

(22) Filed: Jul. 2, 1998

(51) Int. Cl.[7] .................. G01N 27/26; G01N 27/447
(52) U.S. Cl. .................. 436/43; 436/44; 436/174; 436/180; 436/514; 422/63; 422/65; 422/100; 204/451; 204/601; 204/604
(58) Field of Search .................. 422/63, 65, 66, 422/81, 82.01, 82.02, 82.05, 100, 101, 104; 436/43, 44, 149, 514, 174, 180; 204/451, 601, 604; 435/287.2, 288.5

(56) References Cited

U.S. PATENT DOCUMENTS

| | | | | |
|---|---|---|---|---|
| 4,554,839 A | * | 11/1985 | Hewett et al. | 73/864.16 |
| 4,803,050 A | * | 2/1989 | Mack | 422/65 |
| 4,909,920 A | * | 3/1990 | Sarrine et al. | 204/299 |
| 4,938,080 A | * | 7/1990 | Sarrine et al. | 73/861.21 |
| 4,952,518 A | * | 8/1990 | Johnson et al. | 436/518 |
| 5,096,670 A | * | 3/1992 | Harris et al. | 422/65 |
| 5,108,703 A | * | 4/1992 | Pfost et al. | 422/65 |
| 5,274,240 A | | 12/1993 | Mathies et al. | 250/458.1 |
| 5,376,252 A | | 12/1994 | Ekstrom et al. | 204/299 R |
| 5,460,709 A | | 10/1995 | Sarrine et al. | 204/299 R |
| 5,500,071 A | | 3/1996 | Kaltenbach et al. | 156/272.8 |
| 5,571,410 A | | 11/1996 | Swedberg et al. | 210/198.2 |
| 5,587,128 A | * | 12/1996 | Wilding et al. | 422/50 |
| 5,681,484 A | | 10/1997 | Zanzucchi et al. | 216/2 |
| 5,716,825 A | * | 2/1998 | Hancock et al. | 435/286.5 |
| 5,858,195 A | * | 1/1999 | Ramsey | 204/601 |

(List continued on next page.)

FOREIGN PATENT DOCUMENTS

JP  10148628 A  *  6/1998  ......... G01N/27/447

OTHER PUBLICATIONS

A. T. Woolley et al., "High–Speed DNA Geotyping Using Microfabricated Capillary Array Electrophoresis Chips", Anal. Chem., 69:2181–2186 (1997).

(List continued on next page.)

Primary Examiner—Jill Warden
Assistant Examiner—Kathryn Bex
(74) Attorney, Agent, or Firm—Yonggang J.; Royal N. Ronning, Jr.

(57) ABSTRACT

A substrate with a plurality of microchannels is movably deployed with other movable objects that will load sample into the microchannels, stimulate molecular migration, read the results of the migration, remove and replace the substrate, and prepare for a new run. The other objects include a gripper for engaging and moving the substrate, an electrode array of fine wires suitable for fitting into the microchannels for electromigration, and a scanning detector for reading migration results. A sequence of automatic operations is established so that one substrate after another may be moved into position, loaded with sample, stimulated for molecular migration, read with a beam, and then removed and replaced with a fresh substrate.

18 Claims, 14 Drawing Sheets

U.S. PATENT DOCUMENTS

| | | | | |
|---|---|---|---|---|
| 5,872,010 A | * | 2/1999 | Karger et al. | 436/173 |
| 5,885,430 A | * | 3/1999 | Kernan et al. | 204/451 |
| 5,906,723 A | * | 5/1999 | Mathies et al. | 204/603 |
| 6,013,168 A | * | 1/2000 | Arai | 204/601 |
| 6,100,535 A | * | 8/2000 | Mathies et al. | 250/458.1 |
| 6,132,582 A | * | 10/2000 | King et al. | 204/453 |
| 6,143,152 A | * | 11/2000 | Simpson et al. | 204/451 |
| 6,207,031 B1 | * | 3/2001 | Adourian et al. | 204/450 |
| 6,231,813 B1 | * | 5/2001 | Ally et al. | 204/456 |

OTHER PUBLICATIONS

A. T. Woolley et al., "Ultra–High–Speed DNA Sequencing Using Capillary Electrophoresis Chips", Anal. Chem., 67:3676–3680 (1995).

P. C. Simpson et al., "High–throughput genetic analysis using microfabricated 96–sample capillary array electrophoresis microplates", Proc. Natl. Acad. Sci. USA, 95:2256–2261 (1998).

R. M. McCormick et al., "Microchannel electrophoretic separation of DNA in injection–molded plastic substrates", Anal. Chem., 69:2626–2630 (1997).

C. Davidson et al., "Development of a Microchannel Based DNA Sequencer", DOE Human Genome Program Contractor–Grantee Workshop VI, Santa Fe, NM (1997).

D. Jed Harrison et al., "Capillary Electrophoresis and Sample Injection Systems Integrated on a Planar Glass Chip", Analytical Chemistry, vol. 64, No. 17, Sep. 1, 1992, pp. 1926–1932.

D. Jed Harrison et al., "Micromachining a Miniaturized Capillary Electrophoresis–Based Chemical Analysis System on a Chip", Science, vol. 261, Aug. 13, 1993, pp. 895–897.

S. Jacobson et al., "Effects of Injection Schemes and Column Geometry on Performance of Microchip Electrophoresis Devices", Anal. Chem., vol. 66, No. 7, Apr. 1, 1994, pp. 1107–1113.

S. Jacobson et al., "High–Speed Separations on a Microchip", Analytical Chemistry, vol. 66, No. 7, Apr. 1, 1994, pp. 1114–1116.

* cited by examiner

ROBOTIC MICROCHANNEL BIOANALYTICAL INSTRUMENT

TECHNICAL FIELD

The invention relates to molecular separation technology and, more particularly, to a robotic instrument for analysis of multiple samples in microchannels.

BACKGROUND ART

In the past ten years or so, parallel capillaries have been used extensively for molecular separations, such as by means of electrophoresis. Capillary electrophoresis has been used for the analysis of DNA and proteins, and for the separation of small ions, small molecules, bacteria, and viruses. Different separation media have been used in the capillaries including solutions, gels, and polymers. In each technique, the mobility of the target can be measured.

Capillaries have been applied both to DNA fragment length analysis and to DNA sequencing. The study of nucleotide sequences relies upon the high resolution separation of polynucleotide fragments. Each fragment in a family of fragments is tagged with fluorescent markers and the differences in the molecular migration in a capillary channel are observed. Fragments having differences of only a single base pair are routinely separated with fluorescent detection.

To increase the throughput, many capillaries can be used in parallel. Parallel channel electrophoresis allows many samples to be analyzed simultaneously and can result in high throughput rates.

Recently, several groups have implemented capillary electrophoresis in microchannel formats (A. T. Wooley, G. F. Sensabaugh and R. A. Mathies, "High-Speed DNA Genotyping Using Microfabricated Capillary Array Electrophoresis Chips", *Anal. Chem.*, 69:2181–2186 (1997); A. T. Woolley and R. A Mathies, *Anal. Chem.*, 67:3676–3680 (1995); A. T. Woolley, P. C. Simpson, S. Liu, R. Johnston, G. F. Sensabaugh, A. N. Glazer, and R. A. Mathies, "Advances in Microfabricated Integrated DNA Analysis Systems", HPCE98 (1998); P. C. Simpson, D. Roach, A. T. Woolley, T. Thorsen, R. Johnston, G. F. Sensabaugh, and R. A. Mathies, "High-throughput genetic analysis using microfabricated 96-sample capillary array electrophoresis microplates", *Proc. Natl. Acad. Sci. USA*, 95:2256–2261 (1998). This approach uses microchannels etched or molded into a substrate as the separation channels in place of capillaries (R. M. McCormick, R. Nelson, M. G. Alonso-Amigo, D. J. Benvegnu and H. H. Hooper, "Microchannel electrophoretic separation of DNA in injection-molded plastic substrates", *Anal. Chem.* 69:2626–2630 (1997); U.S. Pat. No. 5,376,252, issued 1994 to B. Ekstrom, G. Jacobson, O. Ohman and H. Sjodin). The resulting device is commonly called a microchip, even though the physical size of the entire substrate can vary from microchip size, i.e. dimensions of a few millimeters on a side, to wafer size, i.e. dimensions similar to semiconductor wafers (10–20 centimeters diameter) to microchannels in 48 cm long "macrochips" (C. Davidson, J. Balch, L. Brewer, J. Kimbrough, S. Swierkowski, D. Nelson, R. Madabhushi, R. Pastrone, A. Lee, P. McCready, A. Adamson, R. Bruce, R. Mariella and A. Carrano, "Development of a Microchannel Based DNA Sequencer", DOE Human Genome Program Contractor-Grantee Workshop VI, Santa Fe, NM (1997)). The determining factors in microchip size are the complexity of microchannel routes and the lengths of the separation channels. The length of the channels must allow for sample input, sample migration and a measurement zone. The channels are typically of dimensions from 8 to 40 micrometers deep and 30 to 150 micrometers wide. The small channels resolve DNA fragments in significantly shorter times than capillaries with larger cross-sectional area.

Beyond providing parallel capillaries, some advances in speed of analysis have been achieved by providing parallel sample wells and providing automated optical detectors and software analyzers. In spite of these advances, fine separations are still a time consuming and labor intensive process, particularly in handling and presentation of the specimen to an analysis instrument.

An object of the invention was to devise an apparatus for automatic handling and presentation of specimens into microchips and macrochips for parallel high throughput analysis in microchannels. A further object was to automate the presentation of the chips to an analysis station where electrodes would be docked, samples injected into the separation channels, the separations performed, and the samples detected.

SUMMARY OF THE INVENTION

The above object has been achieved with a macro to micro interface for loading, handling, running, and analyzing samples in an instrument based upon electrophoresis in microchannels on a microchip. The microchip has macroscale inlet ports leading to the microchannels. The inlet ports are spaced apart to match the size and spacings of pipettors in an array of ganged pipettor tips.

The microchannels provide microscopic volumes, much less than a microliter, in which analysis is carried out. The instrument features a microchip handler, with relative motion of the microchip with respect to a pipettor, electrodes, and detector. In some instances the microchip is moved, while in other instances, the other components are moved. There is a sequence of automatic operations involving placing a sample-free microchip on a chuck, loading samples with a pipetting device into the microchip, contacting microchannels in the microchip with electrodes, injecting samples into the separation microchannels, running an electrophoretic separation, detecting and measuring the separation, and then removing the microchip.

In a preferred embodiment, a microchip, prefilled with separation matrix but not sample, is held in a vacuum chuck which is movable with high precision on a first Y-axis track from a sample loading station to a sample analysis station. The microchannels of the microchip are filled beforehand with a polymer or other matrix that may act as a sieve to enhance sample separation. At the sample loading station, samples can be loaded into the microchip by a multifunctional device, that includes a pipettor. The multifunctional device moves along a transverse X-axis gantry between the sample loading station on the first Y-axis track and tip and sample stations both on a second Y-axis track, parallel to the first Y-axis track. The second track can move pipette tips, reagent trays, microtiter trays containing samples, or other objects automatically into position for use by the multifunctional device. The multifunctional device, carried by the gantry, moves up and down on a Z-axis, perpendicular to the X and Y axes. Motion along all axes is driven by stepper motors so that precise and accurate positioning may be achieved. A servo motor or other actuator systems may be used for precise position control.

The multifunctional device contains a plurality of ganged pipettors, an individual pipettor, and a vacuuming line. The plurality of pipettors is ganged with spacings matching the well spacings on a microtiter plate. The same spacings are used for sample loading inlet ports on the microchip. In this manner, a multiple-channel pipettor can simultaneously load multiple samples into sample inlet ports.

The multifunctional device can be moved initially from the sample loading station on the first track to the tip and sample stations on the second track where new pipette tips are applied to the ganged pipettors. The multifunctional device then moves on the gantry to pickup a tip guide and then moves back to the tip and sample stations on the second track. The second track can then be moved to a position where the ganged pipettors on the gantry can withdraw samples from a microtiter plate on the track. The multifunctional device then moves on the gantry to the sample loading station where it deposits the samples into sample inlet ports in the microchip on the first track. The multifunctional device moves back along the gantry first to release the tip guide and then to the tip and sample station where the used tips are discarded into a used tip tray that has been moved into position below the multifunctional device by the second track. The cycle of picking up tips, tip guide, and samples; delivering the sample to the microchip; and then parking the tip guide and discarding the used tips is repeated until the microchip has been completely loaded.

After the microchip has been loaded, it is moved to the sample analysis station on the first track below a sample analysis detector and raised to dock with the array of wire electrodes supported by a platform over the first track. The final position of the microchip places the microchannels in the focal plane of a detector at the sample analysis station. The detector preferably includes a scanning confocal laser microscope capable of detecting fluorescently tagged molecules during separation.

The electrical potential of the electrodes can be controlled to first move precise sub-microliter volumes of the samples from the loading wells into an injection region of the separation microchannels, and then to stimulate electromigration in the separation microchannels.

As the samples separate in the microchannels, a region of the microchip is monitored, typically by a scanning confocal laser microscope to detect the molecular separations. For DNA sequencing, four fluorescent markers are usually detected for forming four-color electropherograms of the separations. The four-color electropherograms can be processed to ultimately call the bases and determine the DNA sequence of the samples.

BEST MODE FOR CARRYING OUT THE INVENTION

Figure 1:
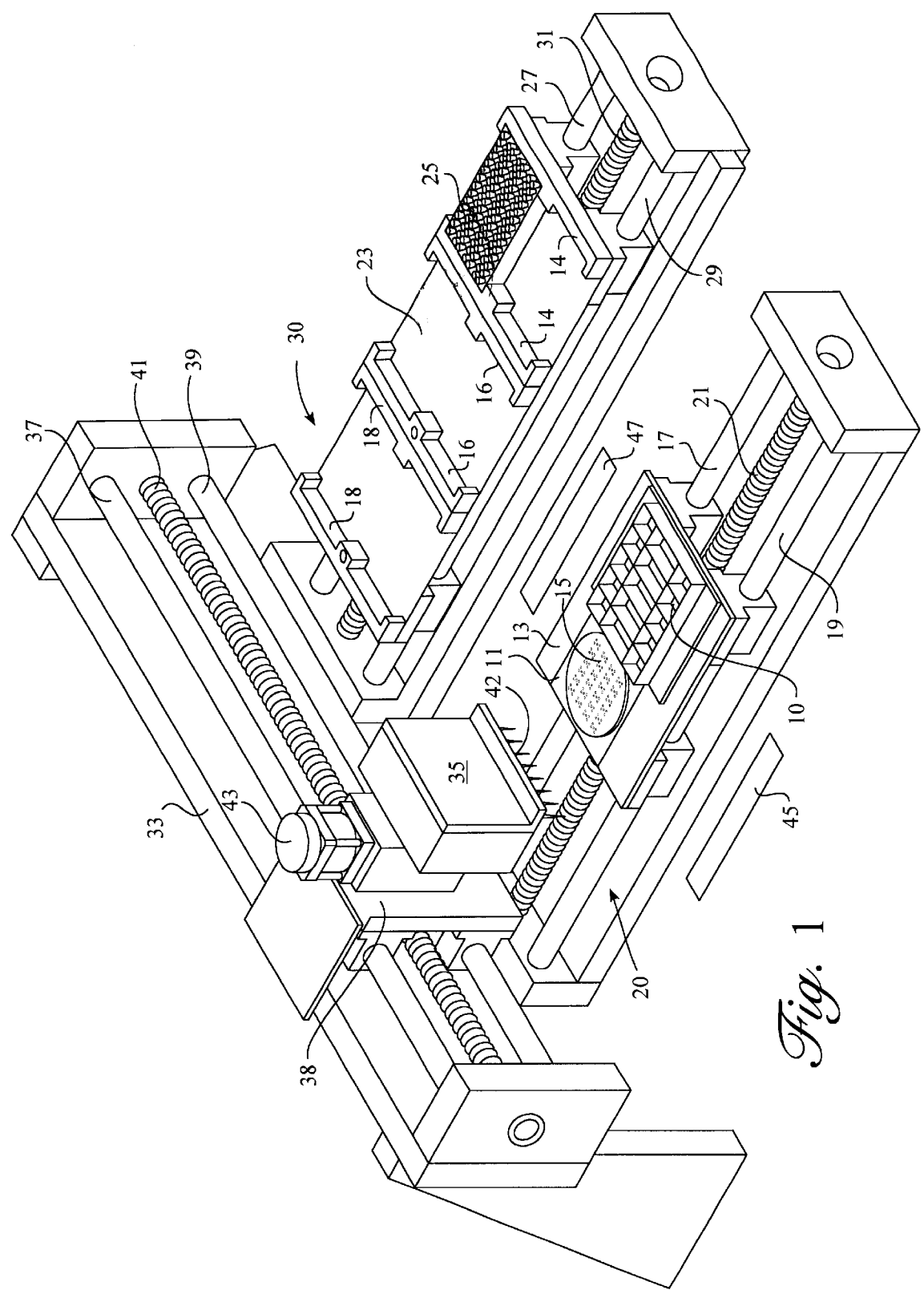
FIG. 1 is a perspective view of the apparatus of the present invention without a sample analysis detector, tip counter, or tip guide.

With reference to FIG. 1, a robotic instrument for microchannel chemical analysis is seen featuring two parallel tracks 20 and 30, with a gantry 33 spanning the parallel tracks. The tracks, 20 and 30, and the gantry 33 are Parker Daedal linear translation stages, well known in the semiconductor equipment field. The first track 20 aligned along a Y-axis, has parallel rails 17 and 19 having a leadscrew 21 midway between. The screw 21 is a precision screw driven by a stepper motor so that a first frame 13, which rides on rails 17 and 19 by means of roller bearings, may be positioned in a desired location. The motor driving the screw is not shown. The roller bearings make contact with the rails 17 and 19 from the first frame 13. By turning screw 21 the first frame 13 may be precisely positioned in a desired location, such as below the multifunctional device 35.

The frame carries a substrate chuck 11, also known in the semiconductor industry as a vacuum chuck for securely holding semiconductor wafers. The substrate chuck 11, adjacent to electrode washing station 10, holds a disk-shaped microchip substrate 15 having microchannels thereon.

As used herein, the term microchip refers to a substrate that contains microchannels. The microchip of the present invention is typically much larger than an integrated circuit microchip. Microchip 15 is shown to be the size of a glass or silicon wafer, with a diameter of about four inches, although larger or smaller devices, or other shapes, may be used. It is not intended that the present invention be limited to any particular size or shape of substrate with microchannels. It is further not intended that the configuration of the microchannels on the microchip be limited to any particular design, but rather that it encompass any geometries, including both two- and three-dimensional microchannels.

As used herein, the term microchannel refers to any channels with cross sectional linear dimensions of less than a millimeter. The microchannels typically have a width in the range of 30 to 150 micrometers and a depth in the range of 5 to 50 micrometers. The microchannels are typically defined therein by microchip manufacturing technology, i.e. masking and etching, although other techniques comprising embossing, micromolding, deposition, and other microfabrication technologies can also be used.

The second track 30, also aligned along a Y-axis, has parallel rails 27 and 29. These rails support the second frame 23 in a low friction rolling relationship. A screw 31 drives the second frame. The second frame carries the microtiter plate 25 as well as other racks or plates which may be seated in holders 14, 16, and 18.

Gantry 33 is a third track, aligned along an X-axis, perpendicular to the Y-axes, having parallel rails 37 and 39, carrying third frame 38 which supports a multifunctional device 35. Screw 41, turned by a stepper motor, not shown, moves the third frame 38 and the multifunctional device 35 between the first track 20 and the second track 30. The multifunctional device functions as a robotic arm carrying a pipettor assembly with a ganged pipettor, an individual pipettor and a vacuum device or other devices.

The multifunctional device 35 can move in the Z-axis, perpendicular to the X and Y axes. Motor 43 moves the multifunctional device 35 with up and down motion in the Z-axis. This motion also moves the pipette tips 42 up and down. Additionally, an air cylinder, not shown, is used to push in a cushioned manner the pipette tips 42 held by the multifunctional device 35 into the microchip, the microtiter plate 25, or the pipette tip racks. The movable pipette tips may be lowered for insertion into the microtiter plate to withdraw samples, then are lifted and moved on the gantry to the second track without interference where they make contact with the microchip for sample loading.

Not shown in FIG. 1 is a detector or measurement instrument, such as a scanning confocal laser microscope, that is located on a platform that stands on pedestal pads 45 and 47, on opposite sides of the first track. The detector sits on a platform above the first frame 13 and is used to induce fluorescence and collect the fluorescence light from microchannels on the microchip.

Figure 2:
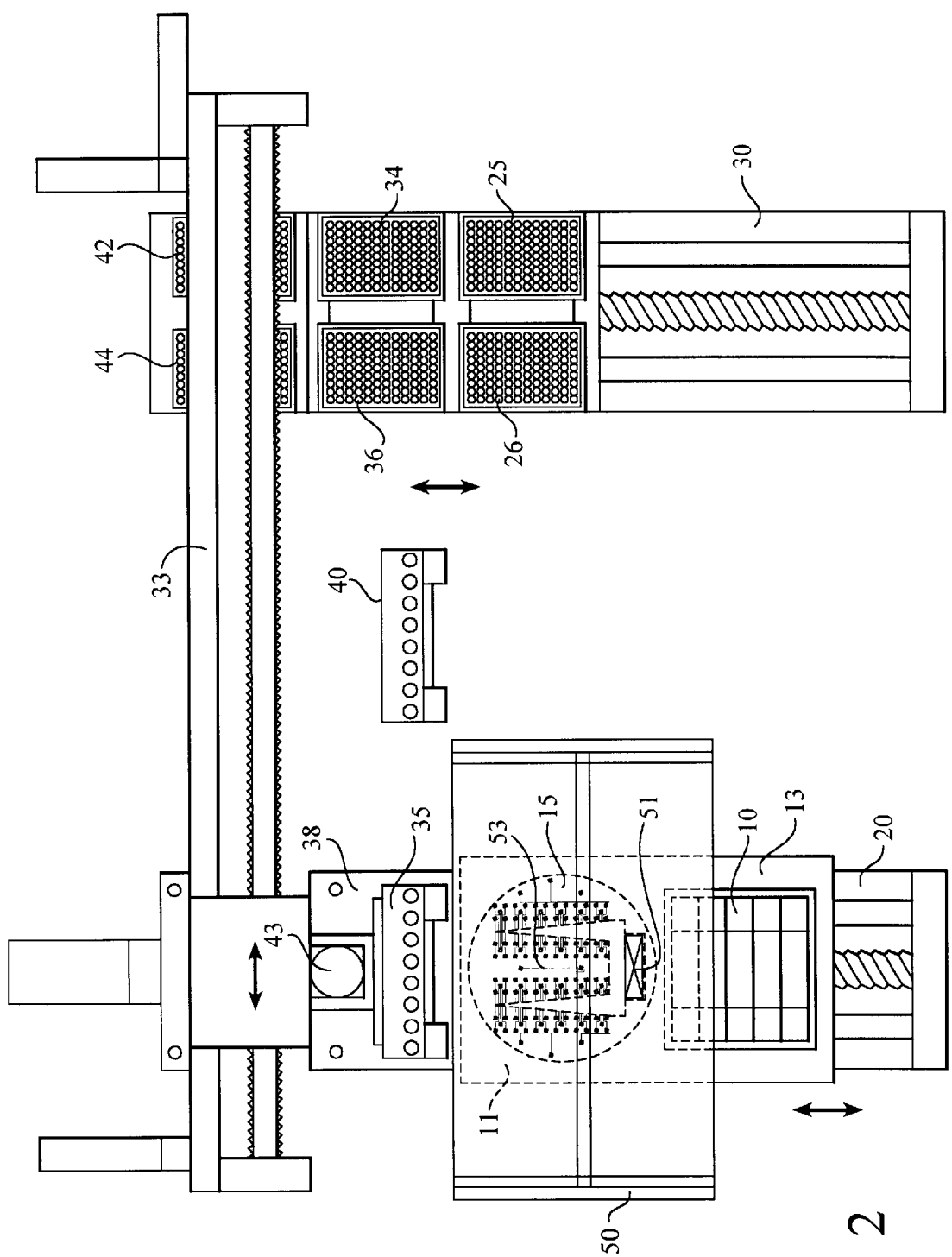
FIG. 2 is a top view of the apparatus of FIG. 1, with a sample analysis detector and tip guide.

With reference to FIG. 2, the first track 20 is spanned by a platform 50, standing on the previously mentioned pedestal pads. The platform 50 carries the array of electrode wires and a sample analysis detector such as a scanning confocal laser microscope. The first frame 13 is advanced to the position of multifunctional device 35 where an array of pipettors carried on the multifunctional device 35 which is attached to third frame 38 dispenses sample material into inlet ports within microchip 15. The pipettors can move up and down along the Z-axis and in a lowered position dispense sample into holes in the microchip. Up and down motion is controlled with the stepper motor 43 which takes the pipettor assembly to its target position. An air cylinder on the multifunctional device actuates the pipettor of interest thereby dispensing samples into the microchip.

The multifunctional device 35, carrying the pipettor array, is movable to the vicinity of the second track 30 where the microtiter plates 25 and 26 reside, as well as fresh pipettor tips in racks 34 and 36. Used tips may be discarded in tip waste racks 42 and 44. The pipettor array on the multifunctional device uses a second air cylinder for attaching new tips and ejecting used tips from the pipettors. After moving to a waste tip rack, the air cylinder behind the pipettor bodies of the pipettor assembly is engaged to push tips off the individual pipettors. To pick up tips, the pipettor assembly is moved over a new tip tray. Then, the stepper motor 43 lowers the multifunctional device 35 near the pipette tips where the air cylinder raises and then abruptly lowers the pipettor assembly with respect to the multifunctional device 35 and provides a spring action to ensure tip pickup from the new tip tray by pushing the tips onto the pipettors. The new tips are held in place by friction engagement.

A second air cylinder actuates the pipettor to pickup and deliver fluids. More material is picked up than is dispensed, thereby reducing the possibility of forming bubbles in the well. Bubbles would interfere with proper current flow in the microchannels.

A tip guide 40 is positioned between the second track 30 and the first track 20. Tip guide 40 is a block having an array of conical holes for allowing entry of pipettor tips. The tip guide is held onto the multifunctional device by vacuum. The tip guide positions tips on the pipettor for precise alignment with the holes in the microchip. The use of the tip guide is optional and is dependent on the design of the microchip.

Figure 3:
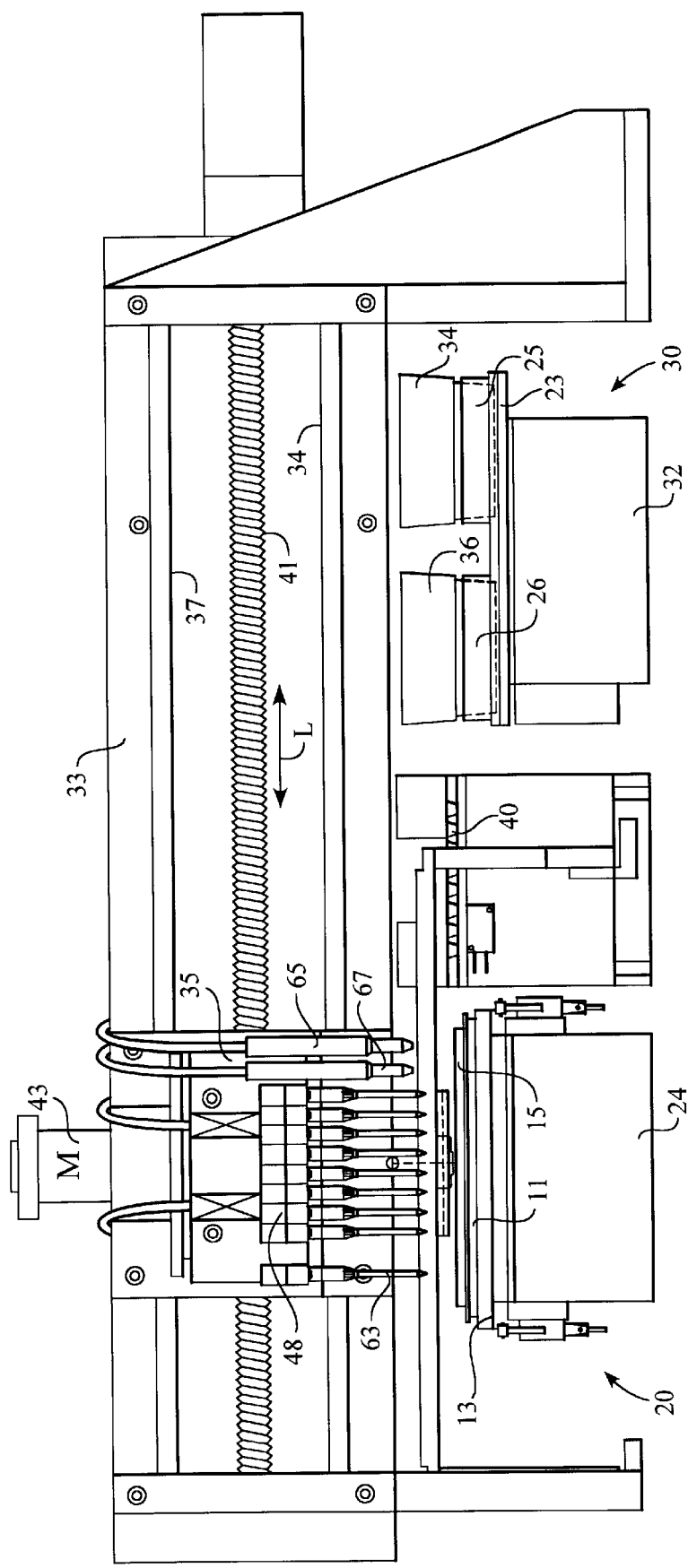
FIG. 3 is a front plan view of the apparatus of FIG. 1 with a tip guide.

With reference to FIG. 3, the first track 20 may be seen to be mounted on a first support table 24 with first frame 13 carrying the substrate chuck 11 and microchip 15 atop the chuck. Multifunctional device 35 is mounted for up and down motion so that pipettor tips can enter holes in the substrate. Gantry 33 allows positioning of the multifunctional device 35 with respect to the first track 20, the tip guide 40, and the second track 30. The second support table 32 holds a second track 30 that carries a second frame 23 bearing microtiter plates 25 and 26, as well as pipette racks 34 and 36. The multifunctional device 35 may move laterally and communicate with microtiter plates 25 and 26. Optical and mechanical position sensors locate the frames on the first and second tracks with respect to the pipettor assembly of the multifunctional device. The controller for the multifunctional device must ascertain the exact positions of the substrate chuck on the first frame, as well as the microtiter plate on the second frame in order to receive and deliver sample to the correct locations.

The multifunctional device 35 is shown to have several other features. It can use a single channel pipettor 63, spaced slightly away from the linear array of ganged pipettors in pipettor assembly 48 to pipette liquids into or out of wells that are not necessarily at the spacings of the ganged pipettor. It has a suction line 65 to remove samples or matrix from the microchip, and a pressure line 67 to move a matrix or to facilitate sample injection as needed. In addition, the multifunctional device 35 can accommodate other means of moving sample into the microchip, such as using a pipetting device with capillaries, microbore tubing, or volumetric devices. The multifunctional device 35 can also be adapted to access a reservoir for bulk pipetting of solutions. A piezoelectric delivery apparatus could also be added if required for precision volumetric control. It is within the scope of the invention that the microchips are loaded by an automated process from a plurality of microchips held in a rack, or hotel, or similar device and that the microtiter plates and racks of pipette tips are also changed by automated mechanisms.

Figure 4:
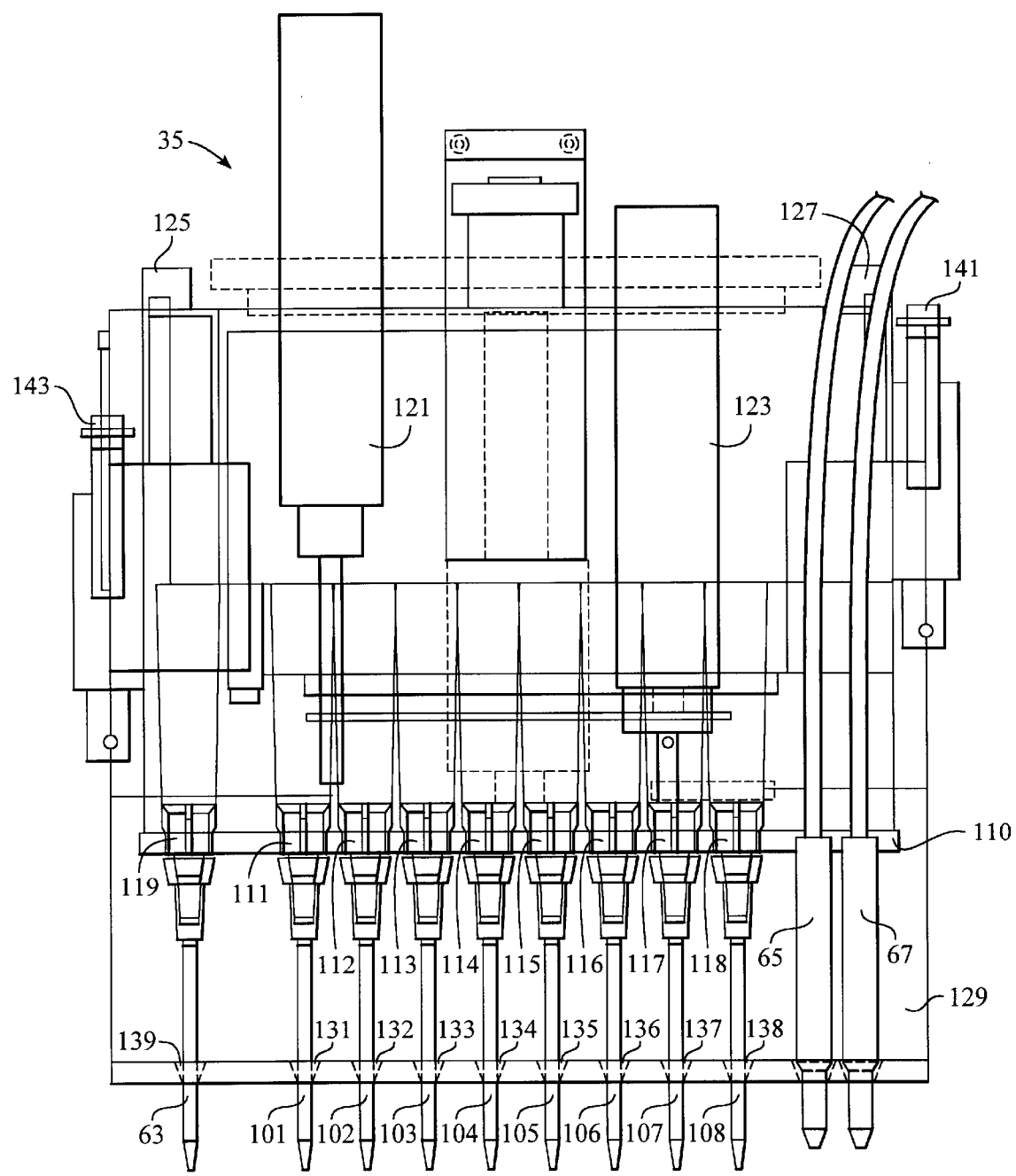
FIG. 4 is a detailed front view of a multifunctional device used in the apparatus of FIG. 1.

With reference to FIG. 4, the multifunctional device 35 is seen to carry an array of individual pipette tips 101–108, plus a single channel pipettor tip 63. When tips are picked up, one to all pipettors are fitted with tips. Each of the tips is connected to a fluid pipetting mechanism which may be a standard Eppendorf pipettor. The pipettors extend through a U-shaped tip ejector 110. The pneumatic cylinder 121 is controlled by an electronic controller for pipetting desired amounts of fluid, on command, through the array of tips 101–108. Microswitches 141 and 143 are mounted on opposite sides of tool 35, at two different elevations, for sensing whether the tool is high or low and signaling the position to other devices. A suction line 65 is mounted at the side of tool 35 for sample or matrix removal from a microchip. A pressure line 67 is used for matrix refilling or to assist with sample injection.

Tip ejector 110 is mounted for up and down motion on short rails with a pair of stops 125 and 127 limiting upward motion of the tip ejector. A pneumatic cylinder 123, connected to a controller, supplies the force for motion of the tip ejector. Tips are ejected when the pneumatic cylinder 123 attempts to raise the tips beyond the tip ejector 110 when tip ejector is stopped against the pair of stops 125 and 127. In this situation, the tips move upwardly, but are stopped against tip ejector 110 and fall off of the pipettor.

The multifunctional device 35 also carries a tip guide 129 which is held in place by suction supplied by a line, not shown, but which suction may be commanded on and off. The tip guide has apertures 131–139 so that the pipette tips are straight from respective pipettors outwardly toward a microchip inlet. The tip guide is an assembly that is picked up from a special location after fresh tips have been attached onto the pipettors, but before the tips are used to withdraw samples from a microtiter plate. Similarly, the tip guide is released before used tips may be discarded into a used tip holder or tray.

Figure 5:
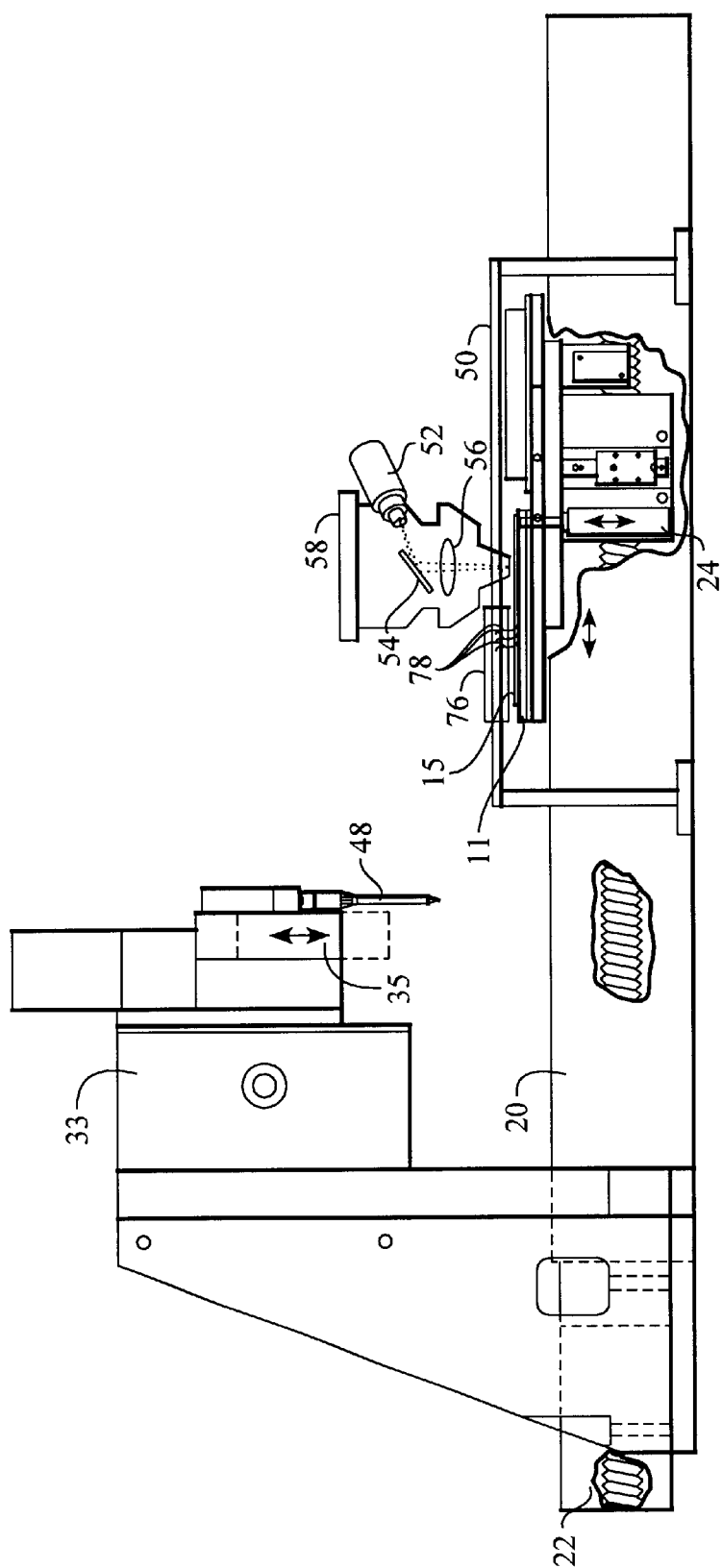
FIG. 5 is a left side view of the apparatus of FIG. 1, with a cutout of the sample analysis station and the detector.

With reference to FIG. 5, at the time of introduction of sample material into microchip 15, the microchip 15 and chuck 11 are moved directly below the pipettors 48 by means of track 20 and its stepper motor and then the pipettor tips 101–108 are lowered into holes in the microchip to deliver sample material. Hole patterns in the microchip match the spacing of tips in the pipettor array, when an array is used. The substrate is able to move under the multifunctional device to different locations using a stepper motor in housing 22 associated with track 20 so that sample material may be delivered to entry holes at various locations.

The microchannels in the microchip are preferably grouped into rows and have eight apertures per row. This allows the array pipettor on the multifunctional device to feed multiple microchannels simultaneously. It is advantageous that sample be delivered simultaneously to eight to twelve, perhaps more, or all sample locations simultaneously until all microchannels have sample. This considerably speeds sample loading for the multiple microchannels. For example, if there are 96 microchannels and 8 pipettor tips, the substrate will need to be moved at least 12 times so that all microchannels will be equipped with sample material. Moreover, the pipettor may need to move laterally while the substrate moves to a position on track 20 so that the pipettor tips will fit into the desired holes in the substrate.

After loading of all the samples, the microchip is then moved to an appropriate position under platform 50. The substrate chuck 11 is raised by pneumatics 24, and an array 78 of fine wires used as electrodes protruding from a circuit board 76, mounted on the underside of platform 50, is automatically inserted into apertures in the microchip. The fine wires are self-supporting stiff wires resembling wafer probe wires used in the semiconductor industry and are used as cathodes and anodes for the separation and to provide other voltages to the microchip. Usually such wires are platinum or other materials with good electrical conductivity and corrosion resistance with diameters typically from 200 micrometers to 500 micrometers.

When certain of the electrodes are connected to appropriate voltage sources, samples can be moved from the sample inlet ports into the separation channels using an electric field; this movement is also referred to as sample injection. The voltage sources are then changed to separate the samples by means of electrophoresis. Typically the microchannels have been pre-loaded with an appropriate separation medium. For example, a separation matrix comprising hydroxyethyl cellulose (HEC) in combination with urea and formamide is disclosed in U.S. Pat. No. 5,534,123 by J. Bashkin, D. Barker and R. Johnston, assigned to the assignee of the present invention.

Once sample migration occurs, the detection region on the microchip is monitored. For fluorescence detection, the excitation light source 52 is selected to have a wavelength that will stimulate fluorescence from target tags. For scanning confocal laser microscope detection, the laser beam excitation light is directed to a galvanometer-based scan mirror 54 that scans the microchip through an objective lens 56, commonly know as a "macro scanning objective". Such objectives have been described for scanning large fields of fluorescent samples; for example, a fluorescence imaging system is described in U.S. Pat. No. 5,719,391 by Robert Kain and assigned to the assignee of the present invention. The objective lens collects emitted fluorescent light from fluorescently tagged target molecules under electrophoretic migration in the microchannels. After intermediate optics, such as a confocal spatial filter and filters to select appropriate wavelengths, photomultiplier tubes 58, CCD arrays, or other photodetectors convert this fluorescence light to electric signals which are collected and processed to form electropherograms.

Figure 6:
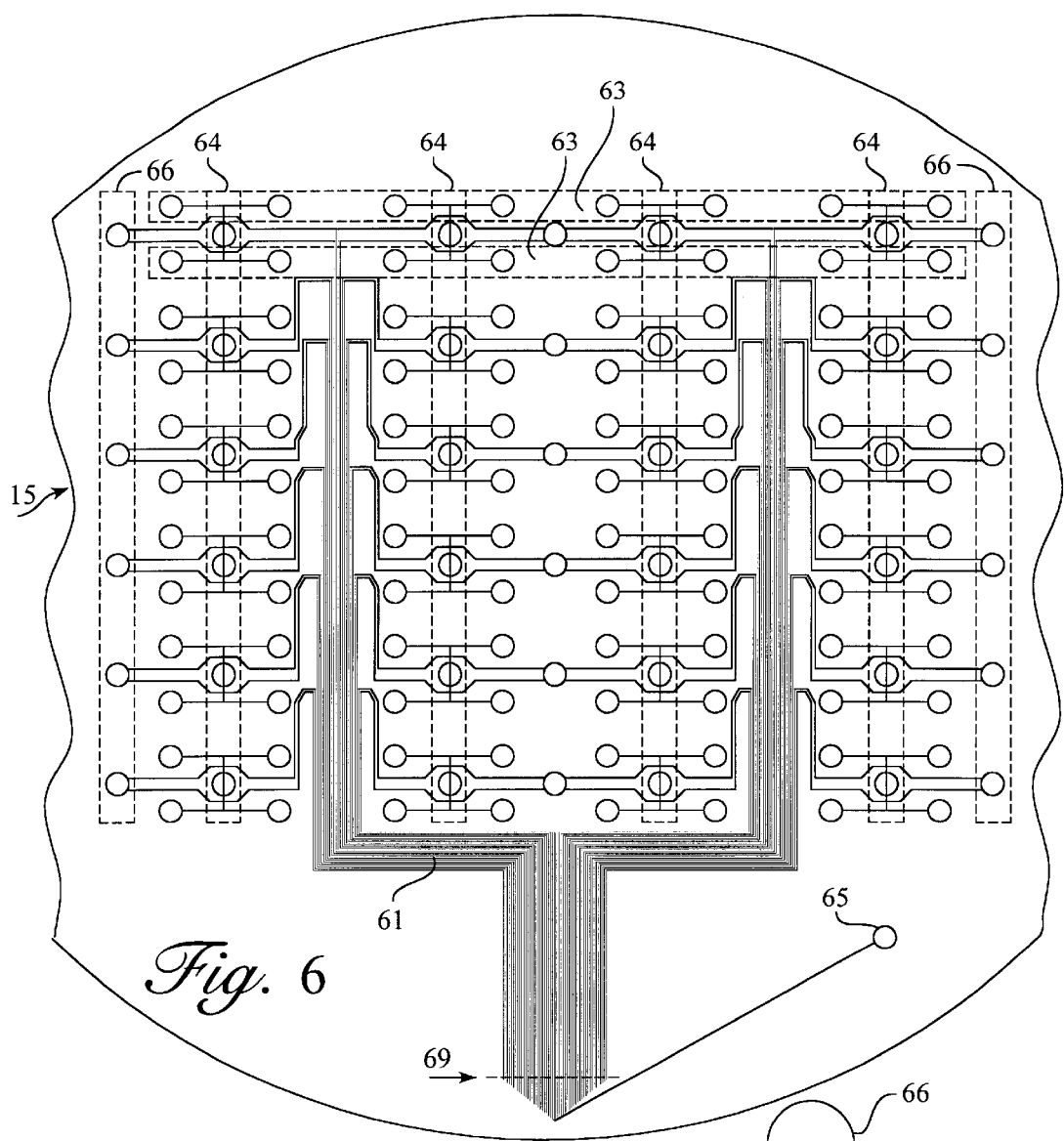
FIG. 6 is a magnified top view of a microchannel structure on a microchip for use in the apparatus of FIG. 1.

With reference to FIG. 6, the microchip 15 is seen to have a plurality of separation microchannels 61 formed in one plate that has been bonded to another plate, not shown. By way of background information, this microchip 15 has been described in P. C. Simpson, D. Roach, A. T. Woolley, T. Thorsen, R. Johnston, G. F. Sensabaugh, and R. A. Mathies, "High-throughput genetic analysis using microfabricated 96-sample capillary array electrophoresis microplates", *Proc. Natl. Acad. Sci. USA*, 95:2256–2261 (1998). The channels have a bottom plate so that fluid cannot escape. The microchannels terminate in open apertures 66 that are used as cathode reservoirs. These reservoirs can either be for each channel or, as shown, may service multiple microchannels. The sample loading reservoirs, two rows being shown in dashed rectangular rows 63, can be large enough for a pipettor tip to enter in order to deliver sample.

In a preferred embodiment, the sample loading reservoirs 63 are connected to waste reservoirs, shown in the dashed rectangular columns 64, by injection microchannels that cross the separation microchannels, as described below. The ends of the separation microchannels merge into a common anode reservoir 65, that is accessible through a hole in the top of the microchip. The sample loading reservoirs 63, waste reservoirs 64, anode reservoir 65, and cathode reservoirs 66 are either individually contacted with electrode wires when the microchip is raised into position or each is individually contacted with electrodes plated onto the surface or within the center of the microchip, terminating at electrically conductive connectors positioned on the edge of the microchip, as shown in FIG. 7.

Figure 7:
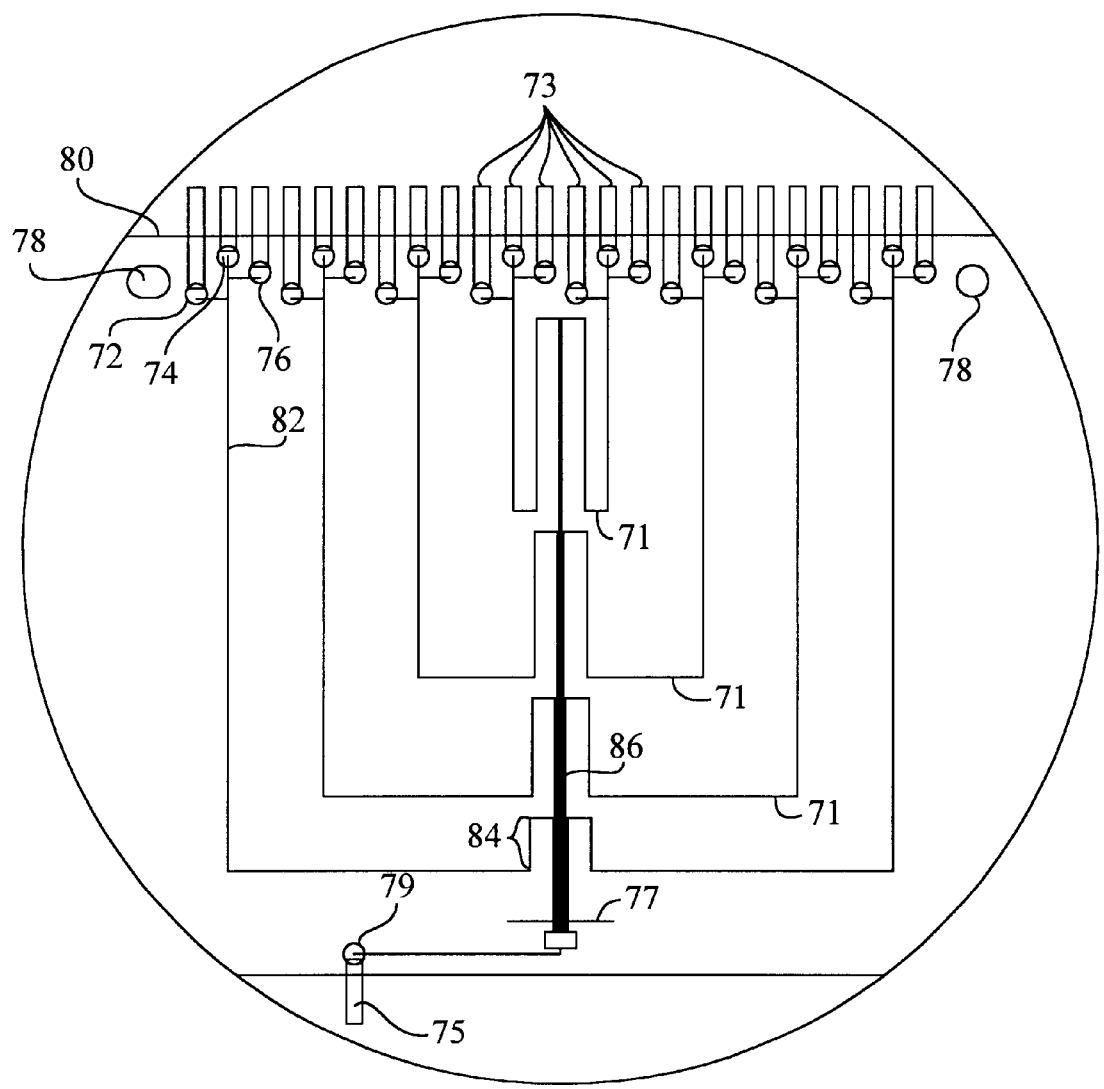
FIGS. 7 and 8 are top views of two alternate embodiments of the structure shown in FIG. 6.

In a preferred embodiment for DNA fragment analysis shown in FIG. 7, the separation microchannels can contain sharp turns 71. While these turns introduce band broadening, the effect is acceptable in a fragment analysis application, such as genotyping. The sharp turns can be used to increase the channel density to up to at least 48 separation channels on a 4" microchip, and can be used to equalize path lengths.

FIG. 7 also illustrates the incorporation of edge electrically conductive connectors 73 and 75 into a microchip. Edge connectors 73 and 75 may be formed by the vapor deposition of metal, such as gold, platinum, or copper, onto glass after the microchannels have been etched, using masking and deposition techniques well known in the semiconductor industry. The edge connectors are flat tabs, like electrical circuit board edge connectors. The edge connectors serve as electrodes and simplify the electrical connection from the microchip to the macroscale. Line 80 indicates where the cover over the substrate terminates, allowing access to the electrical connectors from outside. Below line 80, the substrate has a cover over the electrical terminals where the terminals are not accessible, except through entry ports 72, 74, 76 extending through the cover. A portion of the edge connectors 73 are cathode terminals, while edge connector 75 is an anode terminal. Triplet arrangements of entry ports 72, 74, 76 allow sample movement across a portion of the main microchannel 82 for purposes of injecting sample into the microchannel 82. Microchannel 82 has path bends 84, leading to a main trunk 86 where all microchannels are brought into a parallel array.

In a preferred embodiment, fluorescence detection takes place at scan line 77, an imaginary line, not far from anode port 79 using a scanning confocal laser microscope. Laser scanning at scan line 77 is transverse to the microchannels in the parallel array. Locator holes 78 are used to position the microchip in a desired location.

Figure 8:
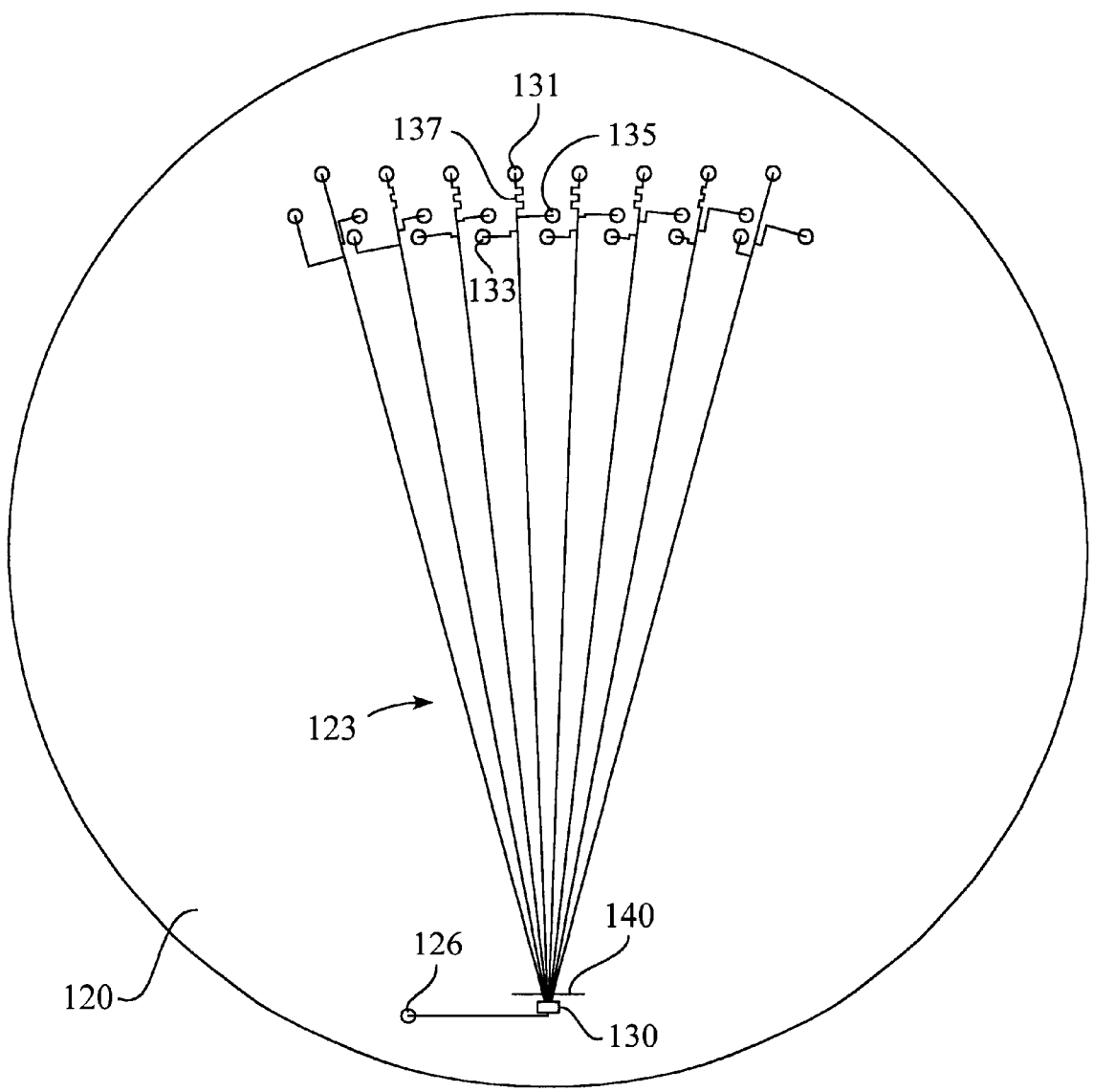

With reference to FIG. 8, a microchip 120 has radially distributed microchannels 123 with a spoke-like pattern considering collector 130 as a hub. The number of microchannels is governed by the size of the microchip. A large array could have microchannels in a 360 degree pattern around a common collector. The microchannels are etched into a glass wafer which is covered with a second flat wafer of similar or identical diameter. Each radial microchannel converges toward a collector 130. The collector is an end reservoir connected to an anode port 126 where an electrode may be inserted. A scan line 140 is an imaginary line where a scanning beam will traverse the converging microchannels, very near the collector 130. The beam, typically a laser beam, will excite fluorescence in the microchannels and the emitted fluorescence will be measured by a detector. Each microchannel has a triplet of inlet ports 131, 133 and 135 for the cathode, waste, and sample reservoirs respectively. The path undulations 137 are introduced for the purpose of path length equalization so that all paths are the same length for electromigration purposes.

A radial configuration of microchannels has the advantages that no bends or turns are present between the injection region and the detection region. The bends or turns degrade the separations and may preclude the high resolution separations required for DNA sequencing.

Figure 9:
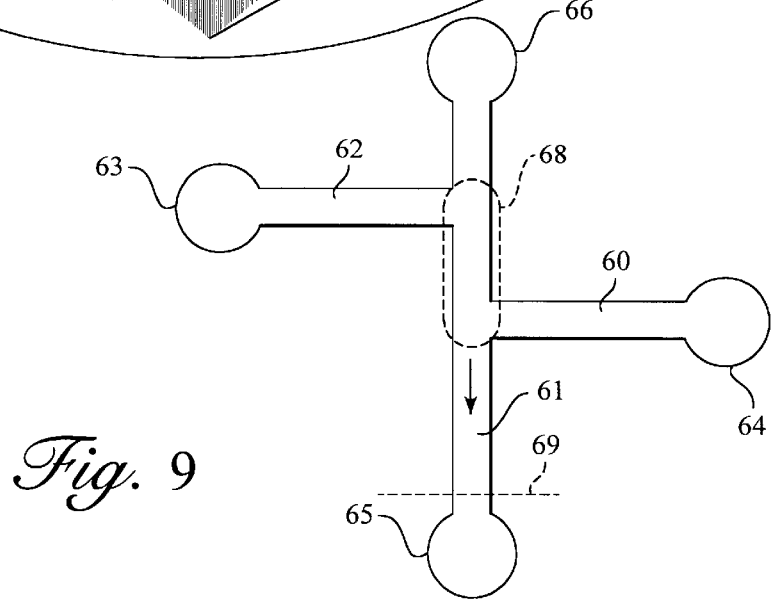
FIG. 9 is a simplified diagram of microchannel paths in the microchips shown in the FIGS. 6–8.

In FIG. 9, a detail of the injector and triplet of inlet ports, shown in FIGS. 6–8, is magnified. Sample reservoir 63 may be seen to have a microchannel path to the waste reservoir 64. Each reservoir has an opening of about 2 mm. in diameter at the surface of a microchip, leading into a microchannel. After all of the samples are loaded in the loading reservoirs 63, samples are moved through the stub microchannel 62 toward the waste reservoir 64 via the second stub microchannel 60 using an electrical potential between the loading reservoir and the waste reservoir. Alternative embodiments may use capillary action, pressure, magnetic, optical trapping, isoelectric focusing, and vacuum injection methods to move the samples into the separation microchannels. Typically, 3 to 5 microliters are inserted into the loading reservoir 63, but the injection region 68 volume only contains from 150 picoliters to 5 nanoliters. This microscopic volume is all that is separated in separation channel 61 under influence of the electric field.

The sequence of events for sample injection in a preferred embodiment is that an injection voltage is applied between each set of sample loading reservoirs 63 and waste reservoirs 64 with a biasing voltage applied to the anode reservoir 65 and cathode reservoirs 66 to prevent sample diffusion into the separation channels 61. The injection voltage is maintained until the sample has moved into the injection region 68 of the microchannels between sample loading reservoirs 63 and waste reservoirs 64 and the separation microchannels 61.

A separation voltage is then applied between the anode reservoir 65 and cathode reservoirs 66 while a back bias is applied to the sample loading reservoirs 63 and waste reservoirs 64 to prevent additional sample from entering the separation microchannels 61. The separation voltage is typically 50 to 300 V/cm and the back bias is typically 90 to 1000 V, depending upon channel lengths. The separation voltage is applied until the samples have passed scan region 69. A typical separation path length from injection region 68 to the detector at scan region 69 is ten centimeters. The detector is located as close as possible to the end of the straight portion of the separation channel 61 so that the maximum separation can be achieved. A typical separation time is five minutes for fragments and five to ten minutes for DNA sequencing.

It is preferable that all paths from the injection region 68 to the anode 65 have equal length and, further, that the paths from the cathode reservoirs 66 to the anode 65 have equal length and that paths from the sample loading reservoirs 63 to the waste reservoirs 64 have equal lengths.

An optical beam from the scanner sweeps across the scan region, illuminating the region and causing fluorescence of tagged target molecules. The scan area of the microchannels is that area where separations are best measured. Target molecules have been tagged with a dye or fluorescent material. When the target molecules are illuminated, optical signals characteristic of the dye, fluorescent tags, or target material will be given off upon stimulation by the scanner that are simultaneously measured by an optical signal detector. Multiple colors or wavelengths are used to distinguish different targets. Presently, for DNA sequencing, four colors are used, corresponding to four nucleotide bases, but any number may be used, depending on the ability of the detector to resolve the different colors, of the beam to generate the fluorescence, and the specific application. For genotyping, one or two colors are typically used, although more colors will allow more samples to be multiplexed per separation channel.

The microchannel arrangement of FIGS. 6–8 allows many channels to be scanned with a single beam scan across the scan region. The beam starts from a known or home position and illuminates each microchannel successively at a known rate of scan. By knowing the scan characteristics, the exact beam position is known and, hence, the identity of the illuminated microchannel is known. The beam spot size is typically ten microns, which is much smaller than the width of the microchannel. Since a large number of separations may be carried out simultaneously, there is a large time savings in analytical operations, such as sequencing. From separation data, the target sample may be identified.

The run is terminated by cessation of applying voltage to the electrodes, the data files are saved, and the vacuum chuck containing the microchip is lowered. The vacuum chuck with the microchip is then moved along first track 20 to the microchip installation position where the microchip is manually removed. The electrode wires are cleaned by moving first track 20, as shown in FIG. 2, until the wash station 10 is positioned below the electrodes. The wash station, containing a cleaning solution, is raised and lowered until the electrodes are cleaned.

Figure 10:
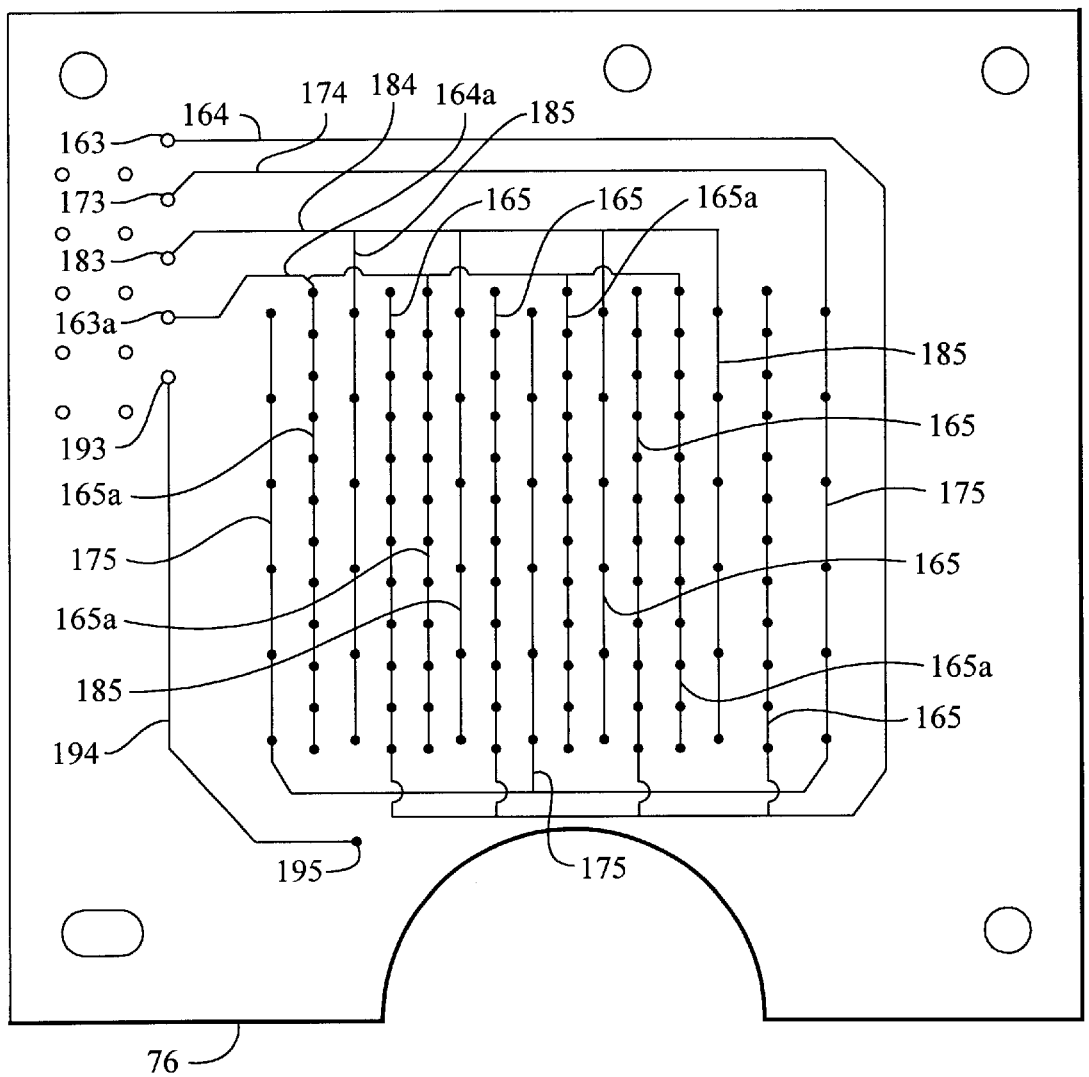
FIG. 10 is a plan of a circuit board showing electrode connections for use in the apparatus of FIG. 1.

With reference to FIG. 10, a circuit board 76 used to support electrodes from the platform over the first track is seen to have five independent wire (or trace) paths 164, 164a, 174, 184 and 194. Each path connects a power terminal to one or more electrode terminals, shown as round dots along a trace. Electrode terminals 163 and 163a are connected to wire traces 164 and 164*a* and to sample terminals 165 and 165*a*. Electrode terminal 173 is connected to wire trace 174 and to cathode reservoir terminals 175. Electrode terminal 183 is connected to wire trace 184 and to waste reservoir terminals 185. Electrode terminal 193 is connected to wire trace 194 and to anode reservoir terminal 195. Note that none of wire traces 164, 164*a*, 174, 184 or 194 intersect another wire trace, but that the wire traces are in mutually insulated relation. The electrode wires previously mentioned are connected to the sample terminals 165 and 165*a*, to the cathode reservoir terminals 175, to the waste reservoir terminals 185 and to the anode reservoir terminal 195, but are not shown in FIG. 10. The wires extend perpendicularly from the circuit board 76 in a self-supporting manner. The circuit board 76 is mounted so that the lower surface of the board is generally parallel with the underside of platform 50 immediately above the microchip to be used for migration measurements and immediately adjacent to the scan region of the microchip.

Appropriate voltages are applied to terminals 163, 163*a*, 173, 183, and 193. The same voltage appears over the length of each connected wire, because the voltage drop over the length of each trace is nil, i.e. the resistance of each trace is very small and only low currents are flowing.

The electronics consists of four modules: motion control, high voltage control, data acquisition, and miscellaneous.

Figure 11:
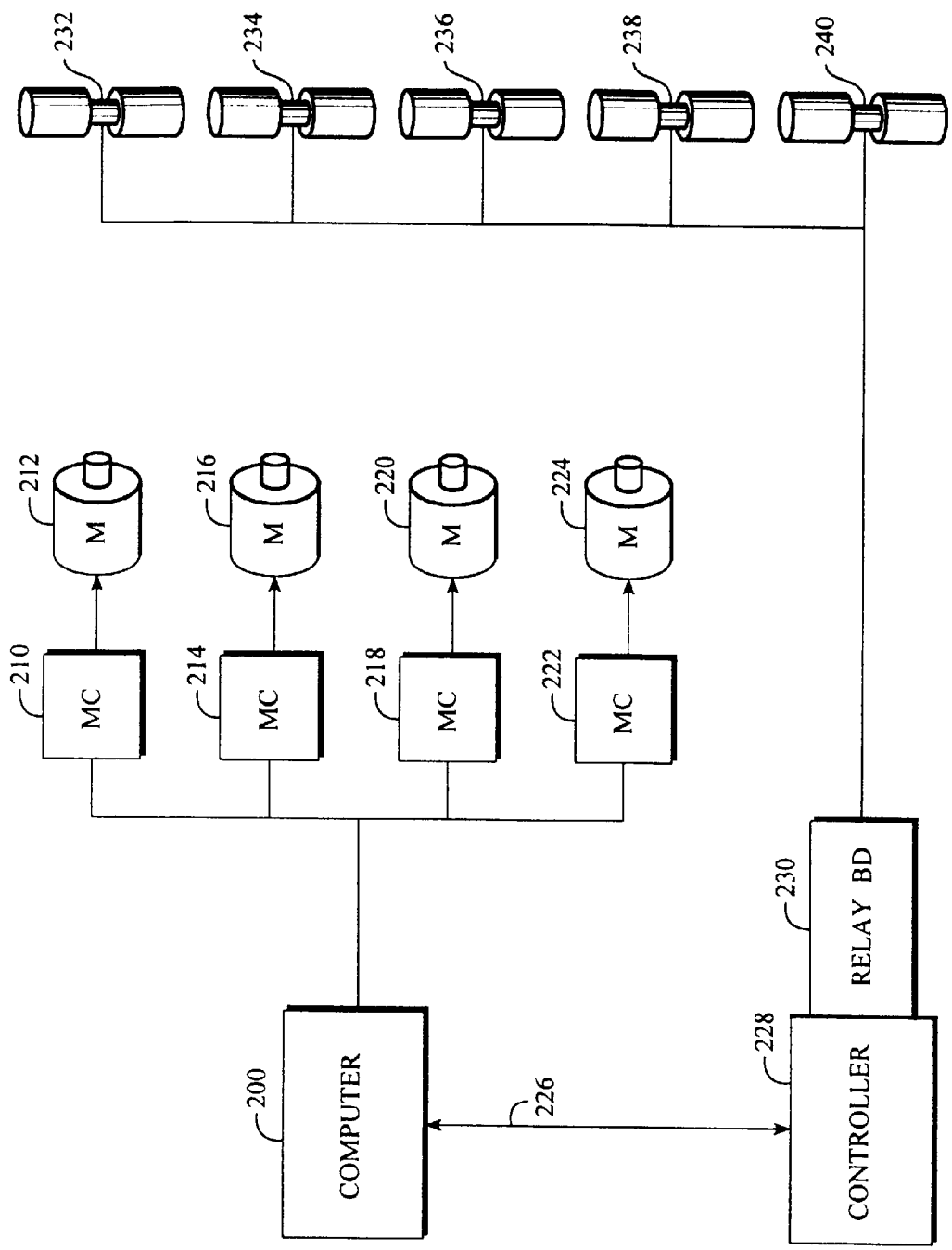
FIG. 11 is an electrical plan for motion control electronics used in the apparatus of FIG. 1.

With reference to FIG. 11, the motion control electronics is controlled by a computer 200, preferably a Windows NT Workstation, that communicates with four motor controllers 210, 214, 218, and 222 via four RS-232 communication ports. Motor controller 210 controls the motor 212 that actuates the gantry in the X-axis. Motor controller 214 controls the motor 216 that actuates the Z-axis. Motor controller 218 controls the motor 220 that actuates the first Y-axis. Motor controller 222 controls the motor 224 that actuates the second Y-axis.

The workstation 200 also communicates via a SCSI bus line 226 with a control module 228 that contains a computer, such as an Intel 386SX embedded controller.

The workstation 200 performs data handling and display functions, while control module 228 only supervises data collection functions. The control module uses a relay board 230 to actuate five pneumatic valves, 232, 234, 236, 238, and 240. Pneumatic valve 232 actuates a cylinder to move the multifunctional device stage down. Pneumatic valve 234 actuates a cylinder to move the multifunctional device stage up. Pneumatic valve 236 actuates a cylinder to move the pipette plunger down. Pneumatic valve 238 actuates a cylinder to move the substrate chuck up. To move the substrate chuck down, the valve 238 releases the pressure and gravity brings the substrate chuck down. Pneumatic valve 240 applies vacuum to hold the tip guide to the multifunctional device or releases the vacuum to release the tip guide. Another manual pneumatic valve, not shown, is used to actuate the vacuum that holds the microchip in the vacuum chuck.

Figure 12:
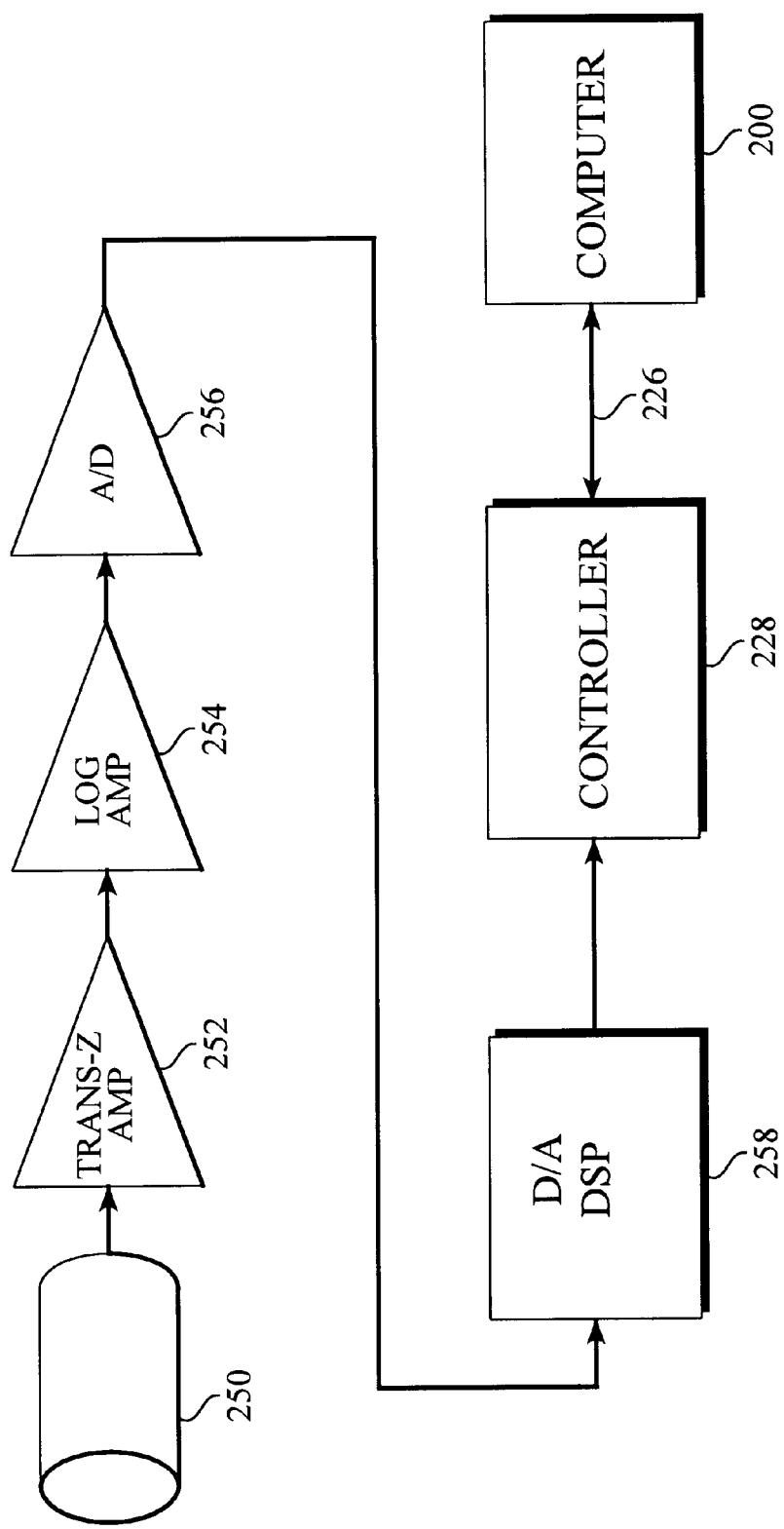
FIG. 12 is an electrical plan for data acquisition electronics used in the apparatus of FIG. 1.

FIG. 12 shows a schematic of the data acquisition electronics. The fluorescence from the sample in the microchip is first detected at a photomultiplier tube 250, such as a Hanamatsu R1477. The photomultiplier bias voltage is controlled to select the output range of the photomultiplier. The output of the photomultiplier is a current, typically in the range of 100 femtoamperes to 100 microamperes. The current is then amplified and converted to a voltage from 0.001 V to 100 V by a transimpedance amplifier 252. The output of the transimpedance amplifier is then converted by a logarithmic amplifier 254 to a logarithmic representation of the data in the range of from greater than 0 V to 10 V. The signal is then passed to a 16-bit analog-to-digital converter 256, such as a Burr-Brown ADS7805 Analog to Digital Convertor which digitizes the signal into 16 bits, giving a dynamic range of 65,536. The output of the analog-to-digital converter 256 is then processed by a digital signal processor 258, such as a Motorola 56000 Digital Signal Processor which first performs an antilogrithmic conversion, then performs a linearity correction based on an internal reference signal input into the transimpedance amplifier 252 at appropriate intervals, and finally, a square root of the signal is performed to compress the signal into 16 bits. The output of the digital signal processor 258 is sent to the aforementioned controller 228 which in turn sends the data to computer 200 via a SCSI communication line 226.

Figure 13:
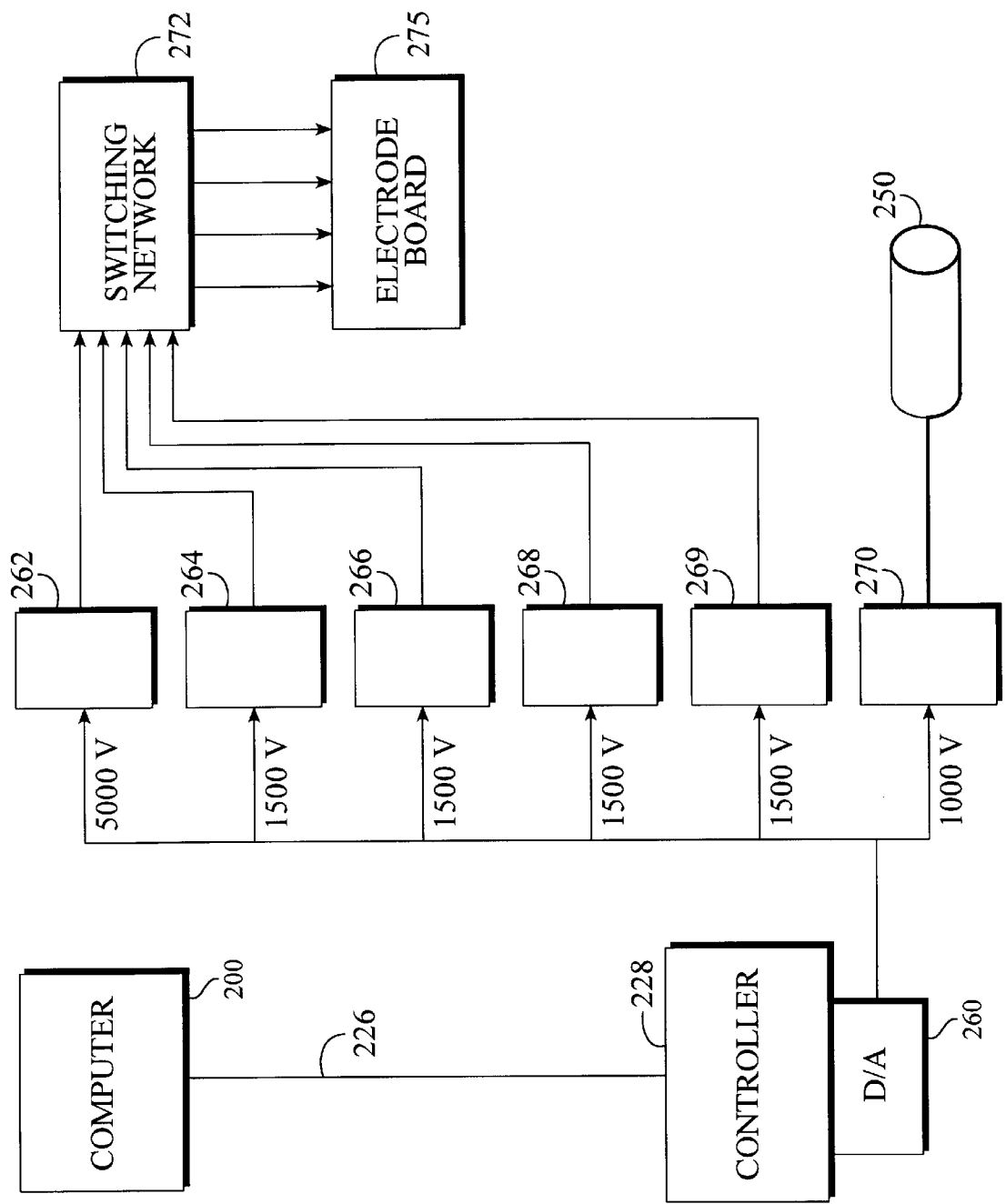
FIG. 13 is an electrical plan for high voltage control used in the apparatus of FIG. 1.

With reference to FIG. 13, the high voltage control electronics is controlled by the computer 200 that communicates with the controller 228 via the SCSI communication line 226. The control module 228 controls a digital-to-analog board 260 that contains six digital-to-analog converters. The digital-to-analog converters control the output voltages of six high voltage power supplies, 262, 264, 266, 268, 269, and 270. The high voltage power supply 270 applies the bias current to the photomultiplier tube 250. The five high voltage power supplies, 262, 264, 266, 268, and 269 are current sources that are connected to the electrode board 275 through a switching network 272. The switching network 272 contains high voltage relays that can select either ground potential as a current sink or a high voltage power supply as a current source. The high voltage power supply 262 can supply up to 5000 V in the preferred embodiment to the electrode board 275 for the anode. The other four high voltage power supplies 264, 266, 268, and 269 can supply up to 1500 V to the cathode, waste, and two sample electrodes respectively.

Figure 14:
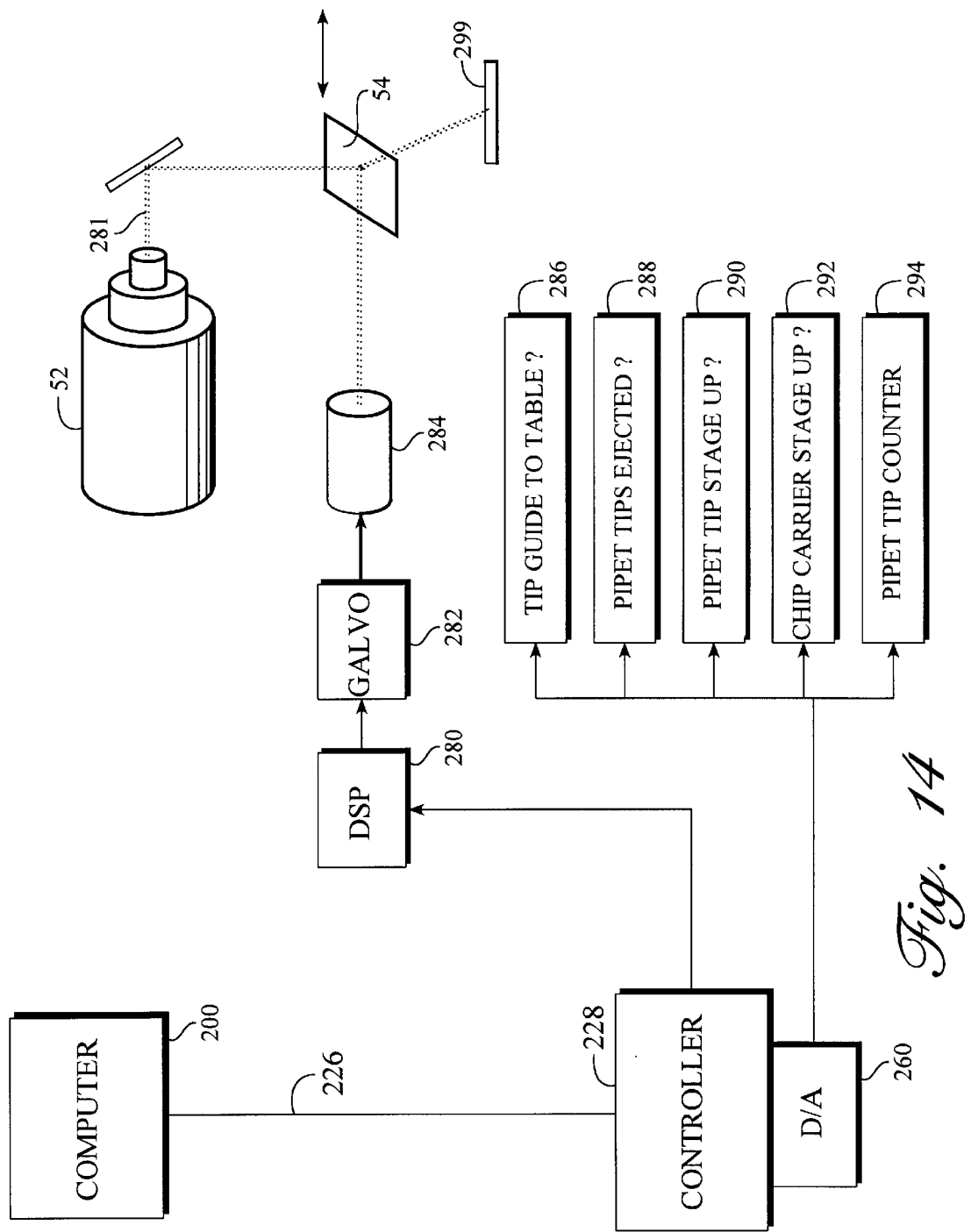
FIG. 14 is an electrical plan for sensors and an optical scanner used in the apparatus of FIG. 1.

With reference to FIG. 14, the high voltage control electronics is controlled by the computer 200 that communicates with the control module 228 via a SCSI communication line 226. The control module 228 controls a digital signal processor 280 that sends voltage pulses to a galvanometer drive board 282. The galvanometer drive board 282 sends voltages to a galvanometer 284, such as a General Scanning G325, with the scan mirror 285 mounted on it. A laser beam 281 from laser 52 is directed onto scan mirror 54. By controlling the galvanometer drive board, the position of the galvanometer can be readily adjusted to perform a line scan across the microchip 299 using beam 281. Alternative embodiments could employ a galvanometer that is controllable in two axes to scan a larger cross-sectional area or to select the optically preferred section of a microchip to scan. The control module 228 controls a digital input board that receives signals from five sensors, 286, 288, 290, 292, and 294. Four of the sensors, 286, 288, 290, and 292, are single pole, single throw switches. Sensor 286 senses if the tip guide is on the table. Sensor 288 senses if the multichannel pipettor has been raised and therefore if the pipette tips have been ejected. Sensor 290 senses if the pipette stage is in the raised position. Sensor 292 senses if the microchip chuck is in the raised position. The pipette tip counter 294 is a through beam light source and detector, such as a Skan-a-matic L60/P60 series subminiature LED-IRED pair, that can sense if the beam has been interrupted. The pipette tip counter 294 is used to count the number of pipettes on the multifunctional device to verify the pickup or release of pipette tips.

The electronics, described in FIGS. 11 to 14, are controlled by software. The control software has six major functional units. The functional units are: (1) Initialize, (2) Load Samples, (3) Load Microchip, (4) Inject Samples, (5) Separate and Scan, and (6) Terminate Run. The functional units can be embodied in programming languages as modules, subroutines, objects, scripts, or other organizations.

The Initialize functional unit prepares the system by initializing the electronics, the stages, the multifunctional device, and the Y-stages. The initialization is comprised of initializing the electronics, homing the stages, initializing the multifunctional device by ejecting any pipette tips and preparing any liquid or microfluidic subsystems, and moving the stages to prepare for sample loading.

The Load Samples functional unit loads samples from reservoirs such as microtiter plates into the microchip. The software controls processing for each plate. The samples from a plate can be looped through by sets of wells that can be simultaneously transferred by the multifunctional device. New pipette tips and the tip guide are picked up. The samples are then loaded into the pipettors from the plates. The multifunctional device is moved to the microchip. At the microchip, the samples are deposited into the sample loading wells. The sets of wells in the plate are then looped through until the microchip has been completely loaded. If the microchip has not been completely loaded, the remaining wells are noted. The sets of wells loaded can be rows, columns, or separated wells. In another embodiment, all the samples might be loaded at once by a simultaneous loading by a device, such as a capillary loader, or from another microchip containing samples, from a piezo electric device with multiple channels, or by other loading strategies.

The Load Microchip functional unit initializes stages as required, moves the loaded microchip into position at the scanner, and docks the microchip at a position in the focal plane of the detector if an optical detection system is employed.

The Inject Samples functional unit is designed to move the samples from the sample loading ports into the injection region of the microchip. The Inject Samples functional unit sets and executes an injection profile that controls the high voltage power to each electrode. A profile specifies the electrode, the voltage potential, and the time for each potential. Simple or complex injection and separation profiles may be employed. In other embodiments, pressure, capillary flow, magnetic fields, or other means can be employed as a profile to move the samples from the sample loading ports into an injector.

The Separate and Scan functional unit performs all functions to separate the injected samples into constituent components for analysis and detection of the components. The high voltage power supplies are first set to the separation profiles. The file name for the data is selected and the data file created. The data acquisition electronics are diagnosed, calibrated, and parameters set; the parameters may include the number of pixels per line, the number of lines, the timing for the data acquisition electronics, or other information. The photomultiplier tube bias voltage is set. There may be multiple photomultiplier tubes as well. The galvanometer is started. The separation profiles are then initiated and voltages applied to the electrodes. The scan is initiated and all the data packets read until the scan parameters have been accomplished. The galvanometer is then stopped, and the voltage to the photomultiplier tube and the power supplies reset to zero or other potentials.

In the Terminate Run functional unit, the stages are initialized as required and then the wash tray is moved under the electrodes. They are then cleaned by moving the wash tray up and down with a pause while the electrodes are immersed in the cleaning solution, which can be water, or have additional components. Alternative embodiments are washing the electrodes with one or a series of liquids or gases or cleaning of the electrodes by heating, plasma treatment, microwave, or other methods to clean the electrodes.

After the Terminate Run functional unit has been executed, the system is ready for another cycle. If another microchip is to be used, the system may start with the Initialization functional unit. Alternatively, if multiple samples are multiplexed into each separation channel, the software might continue at the Inject Samples functional unit, followed by the Separate and Scan, and the Terminate Run functional units.

In the embodiment described above, parallel, spaced apart linear tracks, together with a transverse gantry, were shown to provide the necessary robotic motion to accomplish tasks of loading microchannels with sample and conducting chemical testing and analysis. It is not necessary that a linear format be used.

Figure 15:
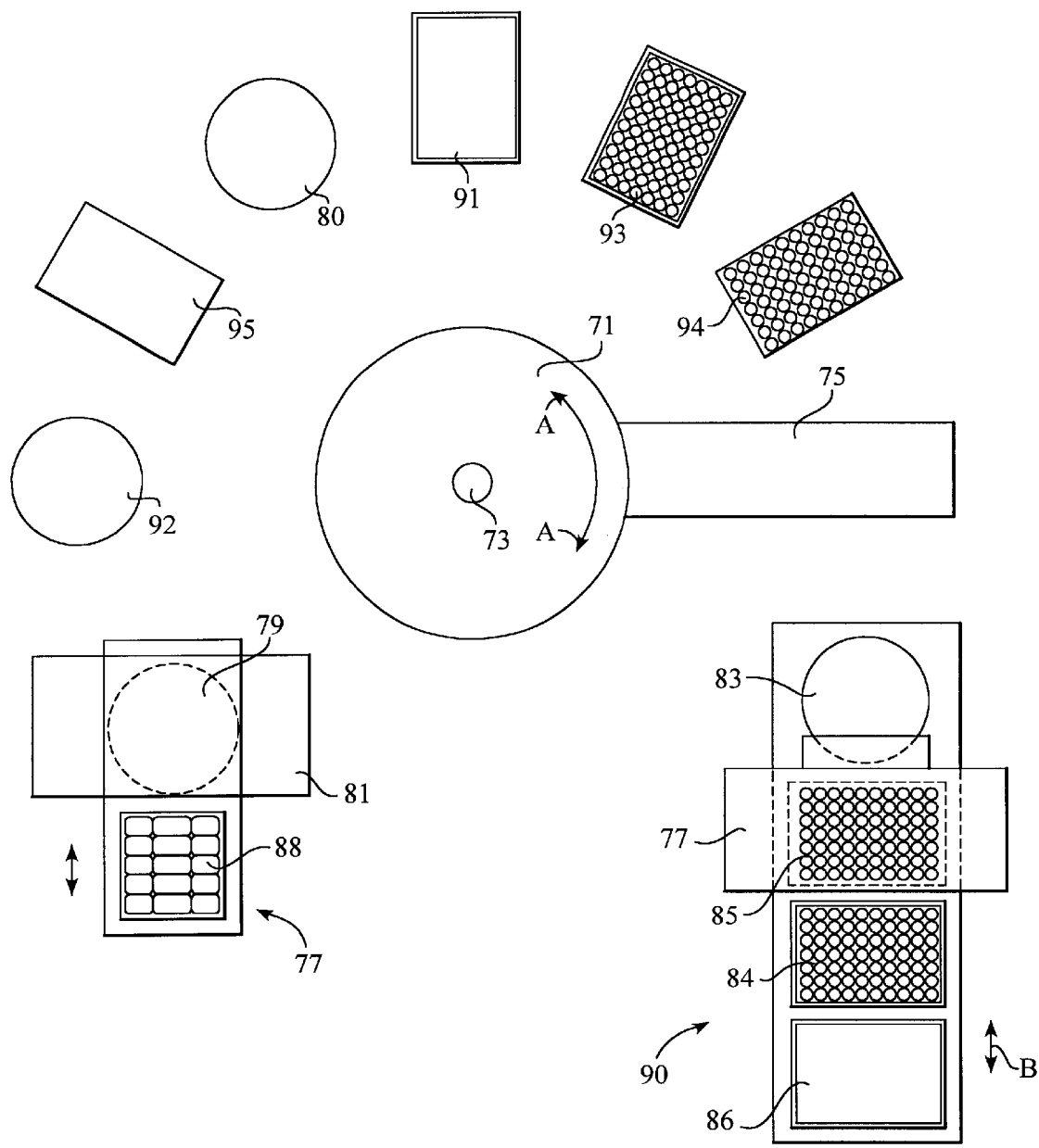
FIG. 15 is a plan view of an alternate embodiment of the apparatus of the present invention.

FIG. 15 shows a rotational format in which a transfer arm robot 71 rotates about a central axis 73, rotating in either direction indicated by arrowheads A. The transfer arm 71 carries a gripper arm 75 having a tool for picking up microchips, as well as a cassette pickup tool for picking cassettes of samples from sample stack 94, new tip cassettes from new tip stack 93, used tip cassettes from used tip stack 91 and wash or other cassettes from stack 95. The transfer arm 71 can swing over a plurality of radially disposed storage locations where these cassettes are stored and move them to loading station 90 which has a linear track allowing motion in reciprocal directions indicated by the arrow B.

Loading station 90 comprising a first frame is spanned by a gantry 77 that mounts a multifunctional tool containing a ganged pipettor capable of up and down motion. New tips are first picked up by the multifunctional tool carried on gantry 77 out of tip rack 84. This requires that the loading station 90 advance the tip rack 84 under gantry 77 so that the ganged pipettor supported on the multifunctional device on the gantry 77 can reach the new tips and push them onto the pipettor. The pipettor is raised and the sample rack 85 is placed below the gantry so that pipettor can move down and pick up desired quantities of sample. Next the microchip at microchip station 83 is moved below the gantry 77 and samples are placed into the holes in the microchip in the manner previously described. The loading sequence is repeated until all microchip wells have been loaded with sample.

Once the microchip at microchip station 83 has been loaded with sample the gripper arm 75 moves the microchip to the analysis station 77 comprising a second frame where a scanner is supported by platform 81. Thereafter, the gripper arm picks another microchip off of the stack at the microchip hotel or cassette 80 and moves it to the microchip station 83 for further processing.

The analysis station 77 can simultaneously analyze a microchip while another is being loaded at the loading station 90. The analysis station 77 also supports electrodes that are inserted into vias or apertures in the microchip which make contact with the liquid in the microchannels for stimulating sample injection and separation as previously described. The appropriate voltages are applied for sample injection and then to stimulate electrophoretic separation while scanning by the scanner, preferable a scanning confocal microscope. When data collection is complete, the stage is moved to position the wash wells 88 beneath the scanner so that the electrodes may be cleaned by rinsing in the wash wells prior to further use and the gripper arm 75 can move the microchip to the used microchip stack 92. Electronics and control software would be similar to that described above.

In this document, when reference is made to a "pipettor", the term should be understood to include, but not be limited to, a single pipettor, a multichannel pipettor, a capillary pipettor or a microfluidic device, a piezoelectric device or other means to move fluids. When reference is made to a "plate", the term should be understood to include, but not be limited to, a microtiter plate, a tube, a microarray device, a reservoir or device that can store or output samples, such as a microfluidic device. Although the main example above relates to electrophoresis, similar apparatus could be used for electrochromatography, gas chromatography, and liquid chromatography. Also, filling of the microchannels is not limited to micropipettor devices. For example, tiny capillaries could be used. Such nonpipettor devices need not match the hole spacing in the microchip.

What is claimed is:

1. Simultaneous chemical analysis in a first microchip substrate, by the method comprising:
    a) providing a microchip substrate defining a plurality of microchannels communicating between opposed cathode and anode ports, said microchip further defining for each microchannel a sample port and a waste port communicating across a segment of said microchannel adjacent said cathode port, and movably mounting the microchannel substrate on a first track at a loading station;
    b) providing a plurality of sample wells, each of said sample wells containing a sample aliquot, and movably mounting the sample wells on a second track;
    c) mounting a multifunctional microchannel loading device on a gantry spanning the first and second tracks, said loading device having a plurality of disengageable pipette tips;
    d) robotically moving said loading device between said plurality of sample wells and said sample ports, and robotically picking up a plurality of said sample aliquots with said plurality of pipette tips, said sample aliquots having detectable target molecules with characteristic migration rates;
    e) robotically delivering said plurality of said sample aliquots simultaneously to said plurality of sample ports, said robotically delivering step further comprising the step of inserting said pipette tips through a corresponding plurality of apertures defined by a tip guide positioned in overlying registry with said sample ports;
    f) repeating steps d) and e) until a desired number of said sample ports have received samples;
    g) robotically moving said first microchip substrate away from said loading station, freeing said loading station for accommodating a replacement microchip substrate;
    h) causing sample separation in the microchannels of said first microchip substrate until desired sample separations are achieved; and
    i) detecting said sample separations in the microchannels at a measurement location.

2. The method of claim 1 further comprising, following step f), robotically replacing said first microchip substrate with said replacement substrate at said loading station.

3. The method of claim 2 wherein robotically replacing said first microchip substrate with said replacement substrate at said loading station includes replacing said first substrate with a replacement substrate which does not have sample included within the substrate.

4. The method of claim 2 further comprising robotically moving said first microchip from said measurement location after detecting said sample separations, freeing said measurement location for said replacement microchip substrate and repeating steps a)–i) using the replacement microchip substrate.

5. The method of claim 4 wherein steps h) and i) are effected using said first microchip substrate at the same time steps d), e), and f) are effected using said replacement microchip substrate.

6. The method of claim 4 further comprising continuously repeating steps a)–h) using a plurality of replacement microchip substrates, wherein steps h) and i) are effected on one of the plurality of said microchip substrates at the same time steps d), e), and f) are effected using another of said microchip substrates.

7. The method of claim 4, further comprising after step f) robotically replacing said sample in said sample wells.

8. The method of claim 1 wherein causing sample separation in the microchannels of said first microchip substrate is effected by robotically moving the chip to place the chip in contact with a plurality of wires such that the contents within a plurality of the individual microchannels on said substrate are brought into contact with an anode wire and a cathode wire and introducing electric current through said microchannel to effect electrophoretic separation.

9. The method of claim 1 wherein said detection is further defined by optically scanning the plurality of microchannels.

10. The method of claim 9 wherein said optically scanning is further defined by confocal optically scanning a plurality of the microchannels.

11. The method of claim 9 wherein providing microchannels in a microchip substrate includes providing microchannels arranged in parallel or at an angle, with a transverse line defining a scan region.

12. The method of claim 1 wherein the step of providing a microchannel loading device comprises providing a plurality of pipettors at spacing equal to the spacing of the sample wells and the inlet ports, said plurality of pipetteors disengageably retaining said plurality of pipette tips.

13. The method of claim 1 wherein providing a microchannel loading device is further defined by providing two parallel tracks having moveable stages, including a first track having a stage for the microchip substrate, and a second track having a stage for the sample wells and for pipettor tips, with the loading device being moveable between the two tracks.

14. The method of claim 1, further comprising the steps of:
    disengaging said plurality of pipette tips; and
    engaging a plurality of replacement pipette tips in substitution for said plurality of pipette tips.

15. The method of claim 14, wherein said engaging step further comprises the step of:
    frictionally engaging and retaining said replacement pipette tips on said loading device.

16. A method for simultaneously separating and detecting DNA sequences of a sample aliquot comprising the steps of:
    providing first microchip substrate defining a plurality of elongate converging microchannels, each said microchannel communicating between opposed cathode and anode ports and each substrate defining a sample port and a waste port communicating across a segment of said microchannel adjacent said cathode port and movably positioning said microchip substrate on a first track at a loading station;

providing a plurality of sample wells, each of said sample wells containing a sample aliquot, and movably positioning said sample wells on a second track;

movably mounting a microchannel loading device on a gantry spanning the first and second tracks, said loading device having a plurality of disengageable pipette tips;

robotically drawing, transporting, and dispensing, from an array of robotically replaceable pipette tips provided on said loading device, a sample aliquot from an array of sample aliquot wells to said sample ports of said microchip substrate;

robotically controlling migration of said sample aliquot from said sample port into said segment of said microchannel;

robotically separating said dispensed portion of said sample aliquots within said segments of the microchannels and causing said separated dispensed portions to migrate towards said anode port of the microchannel; and optically scanning the separated sample at a scanning region of said microchannels and detecting DNA sequences.

17. The method of claim 16, further comprising the step of:

robotically moving said first microchip substrate from said loading station where said sample aliquots are dispensed into said sample ports to an analysis station in registry with a confocal four filament scanner.

18. The method of claim 16, further comprising the step of:

providing a tip guide for precisely guiding said array of pipette tips into fluid communication with said sample ports of said microchip substrate.

* * * * *